(12) United States Patent
Cadman (10) Patent No.: US 7,957,507 B2
(45) Date of Patent: Jun. 7, 2011

(54) METHOD AND APPARATUS FOR MODULATING A RADIATION BEAM

(76) Inventor: Patrick F. Cadman, Saskatoon (CA)

( * ) Notice: Subject to any disclaimer, the term of this patent is extended or adjusted under 35 U.S.C. 154(b) by 86 days.

(21) Appl. No.: 11/361,883

(22) Filed: Feb. 24, 2006

(65) Prior Publication Data

US 2006/0193441 A1    Aug. 31, 2006

Related U.S. Application Data

(60) Provisional application No. 60/657,013, filed on Feb. 28, 2005.

(51) Int. Cl.
*A61N 5/10* (2006.01)
(52) U.S. Cl. .......................................... 378/65; 378/153
(58) Field of Classification Search ................... 378/65, 378/152, 153
See application file for complete search history.

(56) References Cited

U.S. PATENT DOCUMENTS

| | | | |
|---|---|---|---|
| 2,570,820 A * | 10/1951 | Knab | ............................ 378/153 |
| 3,949,265 A | 4/1976 | Holl | |
| 3,964,467 A | 6/1976 | Rose | |
| 4,006,422 A | 2/1977 | Schriber | |
| 4,032,810 A | 6/1977 | Eastham et al. | |
| 4,149,081 A | 4/1979 | Seppi | |
| 4,181,894 A | 1/1980 | Pottier | |
| 4,189,470 A | 2/1980 | Rose | |
| 4,208,185 A | 6/1980 | Sawai et al. | |
| 4,273,867 A | 6/1981 | Lin et al. | |
| 4,314,180 A | 2/1982 | Salisbury | |
| 4,335,465 A | 6/1982 | Christiansen et al. | |
| 4,388,560 A | 6/1983 | Robinson et al. | |
| 4,393,334 A | 7/1983 | Glaser | |
| 4,395,631 A | 7/1983 | Salisbury | |
| 4,401,765 A | 8/1983 | Craig et al. | |
| 4,426,582 A | 1/1984 | Orloff et al. | |
| 4,446,403 A | 5/1984 | Cuomo et al. | |
| 4,480,042 A | 10/1984 | Craig et al. | |
| 4,570,103 A | 2/1986 | Schoen | |
| 4,664,869 A | 5/1987 | Mirzadeh et al. | |
| 4,703,018 A | 10/1987 | Craig et al. | |
| 4,715,056 A * | 12/1987 | Vlasbloem et al. | ........... 378/152 |
| 4,736,106 A | 4/1988 | Kashy et al. | |
| 4,752,692 A | 6/1988 | Jergenson et al. | |

(Continued)

FOREIGN PATENT DOCUMENTS

CA    2091275    9/1993

(Continued)

OTHER PUBLICATIONS

PCT/IB2006/001899 International Search Report and Written Opinion mailed Jan. 5, 2007.

(Continued)

*Primary Examiner* — Chih-Cheng G Kao
(74) *Attorney, Agent, or Firm* — Michael Best & Friedrich LLP (57) ABSTRACT

An apparatus and method to deliver intensity modulated radiation therapy by irradiating a treatment volume with rotation of the radiation beam. The system includes a collimation device comprising a two-dimensional array of pivoting attenuating leaves, which are temporarily placed into the radiation beam path as the gantry rotates around the patient. The leaves are independently movable between a first position and a second position. The radiation beam intensity is modulated by controlling the time that each leaf is present to attenuate the beam.

24 Claims, 8 Drawing Sheets

U.S. PATENT DOCUMENTS

| | | | |
|---|---|---|---|
| 4,754,760 A | 7/1988 | Fukukita et al. | |
| 4,815,446 A | 3/1989 | McIntosh | |
| 4,818,914 A | 4/1989 | Brodie | |
| 4,868,844 A | 9/1989 | Nunan | |
| 4,870,287 A | 9/1989 | Cole et al. | |
| 4,879,518 A | 11/1989 | Broadhurst | |
| 4,912,731 A | 3/1990 | Nardi | |
| 4,936,308 A | 6/1990 | Fukukita et al. | |
| 4,987,309 A | 1/1991 | Klasen et al. | |
| 4,998,268 A | 3/1991 | Winter | |
| 5,003,998 A | 4/1991 | Collett | |
| 5,008,907 A | 4/1991 | Norman et al. | |
| 5,012,111 A | 4/1991 | Ueda | |
| 5,065,315 A | 11/1991 | Garcia | |
| 5,073,913 A | 12/1991 | Martin | |
| 5,084,682 A | 1/1992 | Swenson et al. | |
| 5,107,222 A | 4/1992 | Tsuzuki | |
| 5,124,658 A | 6/1992 | Adler | |
| 5,165,106 A * | 11/1992 | Barthelmes et al. | 378/150 |
| 5,210,414 A | 5/1993 | Wallace et al. | |
| 5,250,388 A | 10/1993 | Schoch, Jr. et al. | |
| 5,317,616 A | 5/1994 | Swerdloff et al. | |
| 5,335,255 A * | 8/1994 | Seppi et al. | 378/4 |
| 5,346,548 A | 9/1994 | Mehta | |
| 5,351,280 A | 9/1994 | Swerdloff et al. | |
| 5,382,914 A | 1/1995 | Hamm et al. | |
| 5,391,139 A | 2/1995 | Edmundson | |
| 5,394,452 A * | 2/1995 | Swerdloff et al. | 378/65 |
| 5,405,309 A | 4/1995 | Carden, Jr. | |
| 5,442,675 A | 8/1995 | Swerdloff et al. | |
| 5,453,310 A | 9/1995 | Andersen et al. | |
| 5,466,587 A | 11/1995 | Fitzpatrick-McElligott et al. | |
| 5,471,516 A | 11/1995 | Nunan | |
| 5,483,122 A | 1/1996 | Derbenev et al. | |
| 5,489,780 A | 2/1996 | Diamondis | |
| 5,523,578 A | 6/1996 | Herskovic | |
| 5,528,650 A | 6/1996 | Swerdloff et al. | |
| 5,548,627 A * | 8/1996 | Swerdloff et al. | 378/65 |
| 5,576,602 A | 11/1996 | Hiramoto et al. | |
| 5,578,909 A | 11/1996 | Billen | |
| 5,581,156 A | 12/1996 | Roberts et al. | |
| 5,596,619 A | 1/1997 | Carol | |
| 5,596,653 A | 1/1997 | Kurokawa | |
| 5,621,779 A | 4/1997 | Hughes et al. | |
| 5,622,187 A | 4/1997 | Carol | |
| 5,625,663 A | 4/1997 | Swerdloff et al. | |
| 5,627,041 A | 5/1997 | Shartle | |
| 5,641,584 A | 6/1997 | Andersen et al. | |
| 5,647,663 A | 7/1997 | Holmes | |
| 5,651,043 A | 7/1997 | Tsuyuki et al. | |
| 5,661,377 A | 8/1997 | Mishin et al. | |
| 5,661,773 A | 8/1997 | Swerdloff et al. | |
| 5,667,803 A | 9/1997 | Paronen et al. | |
| 5,668,371 A | 9/1997 | Deasy et al. | |
| 5,673,300 A | 9/1997 | Reckwerdt et al. | |
| 5,692,507 A | 12/1997 | Seppi et al. | |
| 5,695,443 A | 12/1997 | Brent et al. | |
| 5,712,482 A | 1/1998 | Gaiser et al. | |
| 5,721,123 A | 2/1998 | Hayes et al. | |
| 5,724,400 A | 3/1998 | Swerdloff et al. | |
| 5,729,028 A | 3/1998 | Rose | |
| 5,734,168 A | 3/1998 | Yao | |
| 5,747,254 A | 5/1998 | Pontius | |
| 5,748,703 A * | 5/1998 | Cosman | 378/152 |
| 5,751,781 A | 5/1998 | Brown et al. | |
| 5,753,308 A | 5/1998 | Andersen et al. | |
| 5,754,622 A | 5/1998 | Hughes | |
| 5,754,623 A | 5/1998 | Seki | |
| 5,760,395 A | 6/1998 | Johnstone | |
| 5,771,270 A * | 6/1998 | Archer | 378/150 |
| 5,802,136 A | 9/1998 | Carol | |
| 5,811,944 A | 9/1998 | Sampayan et al. | |
| 5,815,547 A | 9/1998 | Shepherd et al. | |
| 5,818,058 A | 10/1998 | Nakanishi et al. | |
| 5,818,902 A | 10/1998 | Yu | |
| 5,820,553 A | 10/1998 | Hughes | |
| 5,821,051 A | 10/1998 | Androphy et al. | |
| 5,821,705 A | 10/1998 | Caporaso et al. | |
| 5,834,454 A | 11/1998 | Kitano et al. | |
| 5,836,905 A | 11/1998 | Lemelson et al. | |
| 5,842,175 A | 11/1998 | Andros et al. | |
| 5,866,912 A | 2/1999 | Slater et al. | |
| 5,870,447 A | 2/1999 | Powell et al. | |
| 5,870,697 A * | 2/1999 | Chandler et al. | 378/65 |
| 5,877,023 A | 3/1999 | Sautter et al. | |
| 5,877,192 A | 3/1999 | Lindberg et al. | |
| 5,912,134 A | 6/1999 | Shartle | |
| 5,920,601 A | 7/1999 | Nigg et al. | |
| 5,953,461 A | 9/1999 | Yamada | |
| 5,962,995 A | 10/1999 | Avnery | |
| 5,963,615 A | 10/1999 | Egley et al. | |
| 5,969,367 A | 10/1999 | Hiramoto et al. | |
| 5,977,100 A | 11/1999 | Kitano et al. | |
| 5,983,424 A | 11/1999 | Naslund | |
| 5,986,274 A | 11/1999 | Akiyama et al. | |
| 6,011,825 A | 1/2000 | Welch et al. | |
| 6,020,135 A | 2/2000 | Levine et al. | |
| 6,020,538 A | 2/2000 | Han et al. | |
| 6,029,079 A | 2/2000 | Cox et al. | |
| 6,038,283 A | 3/2000 | Carol et al. | |
| 6,049,587 A | 4/2000 | Leksell et al. | |
| 6,066,927 A | 5/2000 | Koudijs | |
| 6,069,459 A | 5/2000 | Koudijs | |
| 6,071,748 A | 6/2000 | Modlin et al. | |
| 6,094,760 A | 8/2000 | Nonaka et al. | |
| 6,127,688 A | 10/2000 | Wu | |
| 6,152,599 A | 11/2000 | Salter | |
| 6,171,798 B1 | 1/2001 | Levine et al. | |
| 6,178,345 B1 | 1/2001 | Vilsmeier et al. | |
| 6,197,328 B1 | 3/2001 | Yanagawa | |
| 6,198,957 B1 | 3/2001 | Green | |
| 6,200,959 B1 | 3/2001 | Haynes et al. | |
| 6,204,510 B1 | 3/2001 | Ohkawa | |
| 6,207,400 B1 | 3/2001 | Kwon | |
| 6,218,675 B1 | 4/2001 | Akiyama et al. | |
| 6,222,905 B1 | 4/2001 | Yoda et al. | |
| 6,241,670 B1 | 6/2001 | Nambu | |
| 6,242,747 B1 | 6/2001 | Sugitani et al. | |
| 6,264,825 B1 | 7/2001 | Blackburn et al. | |
| 6,265,837 B1 | 7/2001 | Akiyama et al. | |
| 6,279,579 B1 | 8/2001 | Riaziat et al. | |
| 6,291,823 B1 | 9/2001 | Doyle et al. | |
| 6,316,776 B1 | 11/2001 | Hiramoto et al. | |
| 6,319,469 B1 | 11/2001 | Mian et al. | |
| 6,322,249 B1 | 11/2001 | Wofford et al. | |
| 6,331,194 B1 | 12/2001 | Elizondo-Decanini et al. | |
| 6,345,114 B1 | 2/2002 | Mackie et al. | |
| 6,360,116 B1 | 3/2002 | Jackson, Jr. et al. | |
| 6,385,286 B1 | 5/2002 | Fitchard et al. | |
| 6,385,288 B1 | 5/2002 | Kanematsu | |
| 6,393,096 B1 | 5/2002 | Carol et al. | |
| 6,405,072 B1 | 6/2002 | Cosman | |
| 6,407,505 B1 | 6/2002 | Bertsche | |
| 6,417,178 B1 | 7/2002 | Klunk et al. | |
| 6,424,856 B1 | 7/2002 | Vilsmeier et al. | |
| 6,428,547 B1 | 8/2002 | Vilsmeier et al. | |
| 6,433,349 B2 | 8/2002 | Akiyama et al. | |
| 6,438,202 B1 | 8/2002 | Olivera et al. | |
| 6,455,844 B1 | 9/2002 | Meyer | |
| 6,462,490 B1 | 10/2002 | Matsuda et al. | |
| 6,465,957 B1 | 10/2002 | Whitham et al. | |
| 6,466,644 B1 | 10/2002 | Hughes et al. | |
| 6,469,058 B1 | 10/2002 | Grove et al. | |
| 6,472,834 B2 | 10/2002 | Hiramoto et al. | |
| 6,473,490 B1 | 10/2002 | Siochi | |
| 6,475,994 B2 | 11/2002 | Tomalia et al. | |
| 6,482,604 B2 | 11/2002 | Kwon | |
| 6,484,144 B2 | 11/2002 | Martin et al. | |
| 6,487,274 B2 | 11/2002 | Bertsche | |
| 6,493,424 B2 | 12/2002 | Whitham | |
| 6,497,358 B1 | 12/2002 | Walsh | |
| 6,498,011 B2 | 12/2002 | Hohn et al. | |
| 6,500,343 B2 | 12/2002 | Siddiqi | |
| 6,504,899 B2 | 1/2003 | Pugachev et al. | |
| 6,510,199 B1 | 1/2003 | Hughes et al. | |
| 6,512,942 B1 | 1/2003 | Burdette et al. | |
| 6,516,046 B1 | 2/2003 | Frohlich et al. | |

| | | |
|---|---|---|
| 6,527,443 B1 | 3/2003 | Vilsmeier et al. |
| 6,531,449 B2 | 3/2003 | Khojasteh et al. |
| 6,535,837 B1 | 3/2003 | Schach Von Wittenau |
| 6,552,338 B1 | 4/2003 | Doyle |
| 6,558,961 B1 | 5/2003 | Sarphie et al. |
| 6,560,311 B1 | 5/2003 | Shepard et al. |
| 6,562,376 B2 | 5/2003 | Hooper et al. |
| 6,584,174 B2 | 6/2003 | Schubert et al. |
| 6,586,409 B1 | 7/2003 | Wheeler |
| 6,605,297 B2 | 8/2003 | Nadachi et al. |
| 6,611,700 B1 | 8/2003 | Vilsmeier et al. |
| 6,617,768 B1 | 9/2003 | Hansen |
| 6,618,467 B1 * | 9/2003 | Ruchala et al. ................ 378/65 |
| 6,621,889 B1 | 9/2003 | Mostafavi |
| 6,633,686 B1 | 10/2003 | Bakircioglu et al. |
| 6,634,790 B1 | 10/2003 | Salter, Jr. |
| 6,636,622 B2 | 10/2003 | Mackie et al. |
| 6,637,056 B1 | 10/2003 | Tybinkowski et al. |
| 6,646,383 B2 | 11/2003 | Bertsche et al. |
| 6,653,547 B2 | 11/2003 | Akamatsu |
| 6,661,870 B2 | 12/2003 | Kapatoes et al. |
| 6,688,187 B1 | 2/2004 | Masquelier |
| 6,690,965 B1 | 2/2004 | Riaziat et al. |
| 6,697,452 B2 | 2/2004 | Xing |
| 6,705,984 B1 | 3/2004 | Angha |
| 6,713,668 B2 | 3/2004 | Akamatsu |
| 6,713,976 B1 | 3/2004 | Zumoto et al. |
| 6,714,620 B2 | 3/2004 | Caflisch et al. |
| 6,714,629 B2 | 3/2004 | Vilsmeier |
| 6,716,162 B2 | 4/2004 | Hakamata |
| 6,723,334 B1 | 4/2004 | McGee et al. |
| 6,741,674 B2 | 5/2004 | Lee |
| 6,760,402 B2 | 7/2004 | Ghelmansarai |
| 6,774,383 B2 | 8/2004 | Norimine et al. |
| 6,787,771 B2 | 9/2004 | Bashkirov et al. |
| 6,787,983 B2 | 9/2004 | Yamanobe et al. |
| 6,788,764 B2 * | 9/2004 | Saladin et al. ................ 378/152 |
| 6,792,073 B2 | 9/2004 | Deasy et al. |
| 6,796,164 B2 | 9/2004 | McLoughlin et al. |
| 6,800,866 B2 | 10/2004 | Amemiya et al. |
| 6,822,244 B2 | 11/2004 | Beloussov et al. |
| 6,822,247 B2 | 11/2004 | Sasaki |
| 6,838,676 B1 | 1/2005 | Jackson |
| 6,842,502 B2 | 1/2005 | Jaffray et al. |
| 6,844,689 B1 | 1/2005 | Brown et al. |
| 6,871,171 B1 | 3/2005 | Agur et al. |
| 6,873,115 B2 | 3/2005 | Sagawa et al. |
| 6,873,123 B2 | 3/2005 | Marchand et al. |
| 6,878,951 B2 | 4/2005 | Ma |
| 6,882,702 B2 | 4/2005 | Luo |
| 6,882,705 B2 | 4/2005 | Egley et al. |
| 6,888,326 B2 | 5/2005 | Amaldi et al. |
| 6,889,695 B2 | 5/2005 | Pankratov et al. |
| 6,907,282 B2 | 6/2005 | Siochi |
| 6,922,455 B2 | 7/2005 | Jurczyk et al. |
| 6,929,398 B1 | 8/2005 | Tybinkowski et al. |
| 6,936,832 B2 | 8/2005 | Norimine et al. |
| 6,955,464 B1 | 10/2005 | Tybinkowski et al. |
| 6,963,171 B2 | 11/2005 | Sagawa et al. |
| 6,974,254 B2 | 12/2005 | Paliwal et al. |
| 6,984,835 B2 | 1/2006 | Harada |
| 6,990,167 B2 | 1/2006 | Chen |
| 7,015,490 B2 | 3/2006 | Wang et al. |
| 7,046,762 B2 | 5/2006 | Lee |
| 7,051,605 B2 | 5/2006 | Lagraff et al. |
| 7,060,997 B2 | 6/2006 | Norimine et al. |
| 7,077,569 B1 | 7/2006 | Tybinkowski et al. |
| 7,081,619 B2 | 7/2006 | Bashkirov et al. |
| 7,084,410 B2 | 8/2006 | Beloussov et al. |
| 7,087,200 B2 | 8/2006 | Taboas et al. |
| 7,112,924 B2 | 9/2006 | Hanna |
| 7,130,372 B2 | 10/2006 | Kusch et al. |
| 7,154,991 B2 | 12/2006 | Earnst et al. |
| 7,186,986 B2 | 3/2007 | Hinderer et al. |
| 7,186,991 B2 | 3/2007 | Kato et al. |
| 7,203,272 B2 | 4/2007 | Chen |
| 7,209,547 B2 * | 4/2007 | Baier et al. ................ 378/149 |
| 7,221,733 B1 | 5/2007 | Takai et al. |
| 7,252,307 B2 | 8/2007 | Kanbe et al. |
| 7,257,196 B2 | 8/2007 | Brown et al. |
| 7,391,026 B2 | 6/2008 | Trinkaus et al. |
| 2002/0007918 A1 | 1/2002 | Owen et al. |
| 2002/0077545 A1 | 6/2002 | Takahashi et al. |
| 2002/0080915 A1 | 6/2002 | Frohlich |
| 2002/0085668 A1 | 7/2002 | Blumhofer et al. |
| 2002/0091314 A1 | 7/2002 | Schlossbauer et al. |
| 2002/0101959 A1 * | 8/2002 | Kato et al. ................ 378/65 |
| 2002/0115923 A1 | 8/2002 | Erbel |
| 2002/0120986 A1 | 9/2002 | Erbel et al. |
| 2002/0122530 A1 | 9/2002 | Erbel et al. |
| 2002/0136439 A1 | 9/2002 | Ruchala et al. |
| 2002/0150207 A1 | 10/2002 | Kapatoes et al. |
| 2002/0187502 A1 | 12/2002 | Waterman et al. |
| 2002/0193685 A1 | 12/2002 | Mate et al. |
| 2003/0007601 A1 | 1/2003 | Jaffray et al. |
| 2003/0031298 A1 | 2/2003 | Xing |
| 2003/0086527 A1 | 5/2003 | Speiser et al. |
| 2003/0105650 A1 | 6/2003 | Lombardo et al. |
| 2003/0174872 A1 | 9/2003 | Chalana et al. |
| 2004/0010418 A1 | 1/2004 | Buonocore et al. |
| 2004/0068182 A1 | 4/2004 | Misra |
| 2004/0105525 A1 | 6/2004 | Short et al. |
| 2004/0116804 A1 | 6/2004 | Mostafavi |
| 2004/0165696 A1 | 8/2004 | Lee |
| 2004/0202280 A1 | 10/2004 | Besson |
| 2004/0230115 A1 | 11/2004 | Scarantino et al. |
| 2004/0254492 A1 | 12/2004 | Zhang et al. |
| 2004/0254773 A1 | 12/2004 | Zhang et al. |
| 2004/0264640 A1 | 12/2004 | Myles |
| 2005/0013406 A1 | 1/2005 | Dyk et al. |
| 2005/0031181 A1 | 2/2005 | Bi et al. |
| 2005/0080332 A1 | 4/2005 | Shiu et al. |
| 2005/0096515 A1 | 5/2005 | Geng |
| 2005/0117707 A1 | 6/2005 | Baier et al. |
| 2005/0123092 A1 | 6/2005 | Mistretta et al. |
| 2005/0143965 A1 | 6/2005 | Failla et al. |
| 2005/0180544 A1 | 8/2005 | Sauer et al. |
| 2005/0197564 A1 | 9/2005 | Dempsey |
| 2005/0251029 A1 | 11/2005 | Khamene et al. |
| 2006/0074292 A1 | 4/2006 | Thomson et al. |
| 2006/0083349 A1 | 4/2006 | Harari et al. |
| 2006/0100738 A1 | 5/2006 | Alsafadi et al. |
| 2006/0133568 A1 | 6/2006 | Moore |
| 2006/0193429 A1 | 8/2006 | Chen |
| 2006/0193441 A1 | 8/2006 | Cadman |
| 2006/0285639 A1 | 12/2006 | Olivera et al. |
| 2007/0041494 A1 | 2/2007 | Ruchala et al. |
| 2007/0041495 A1 | 2/2007 | Olivera et al. |
| 2007/0041497 A1 | 2/2007 | Schnarr et al. |
| 2007/0041498 A1 | 2/2007 | Olivera et al. |
| 2007/0041499 A1 | 2/2007 | Lu et al. |
| 2007/0041500 A1 | 2/2007 | Olivera et al. |
| 2007/0043286 A1 | 2/2007 | Lu et al. |
| 2007/0076846 A1 | 4/2007 | Ruchala et al. |
| 2007/0088573 A1 | 4/2007 | Ruchala et al. |
| 2007/0104316 A1 | 5/2007 | Ruchala et al. |
| 2007/0127623 A1 | 6/2007 | Goldman et al. |
| 2007/0189591 A1 | 8/2007 | Lu et al. |
| 2007/0195922 A1 | 8/2007 | Mackie et al. |
| 2007/0195929 A1 | 8/2007 | Ruchala et al. |
| 2007/0195930 A1 | 8/2007 | Kapatoes et al. |
| 2007/0201613 A1 | 8/2007 | Lu et al. |
| 2007/0211857 A1 | 9/2007 | Urano et al. |

FOREIGN PATENT DOCUMENTS

| | | |
|---|---|---|
| CA | 2180227 | 12/1996 |
| DE | 10221634 | 12/2003 |
| EP | 0259989 | 3/1988 |
| WO | 03/076003 | 9/2003 |
| WO | 2004057515 | 7/2004 |

OTHER PUBLICATIONS

Ronald D. Rogus et al., "Accuracy of a Photogrammetry-Based Patient Positioning and Monitoring System for Radiation Therapy," Medical Physics, vol. 26, Issue 5, May 1999.

D. Rueckert et al., "Nonrigid Registration Using Free-Form Deformations: Application to Breast MR Images," IEEE Transactions on Medical Imaging, vol. 18, No. 8, Aug. 1999.

Yuan-Nan Young, "Registraion-Based Morphing of Active Contours for Segmentation of CT Scans," Mathematical Biosciences and Engineering, vol. 2, No. 1, Jan. 2005.

Anthony Yezzi et al., "A Variational Framework for Joint Segmentation and Registration," Mathematical Method in Biomedical Image Analysis, 2001. (Note: the title of the periodical and the date listed are from the International Search Report, however they do not appear on the article itself.).

Ruchala, Kenneth, et al., "Adaptive IMRT with Tomotherapy", RT Image, vol. 14, No. 25, pp. 14-18, Jun. 18, 2001.

Marcelo Bertalmio, et al., "Morphing Active Contours", IEEE Transactions on Pattern Analysis and Machine Intelligence, vol. 22, No. 7, pp. 733-737, Jul. 2000.

Lu, W., et al., "Automatic Re-Contouring in 4D Radiotherapy", Physical Medical Biology, 2006, Mar. 7, 51(5): 1077-99.

Lu, W., et al., 2004 Automatic Re-Contouring for 4-D Planning and Adaptive Radiotherapy, The 90th RSNA Meeting, Chicago, Illnois, (abstract: Radiology 227 p. 543), (2004).

Lu, W., et al., 2004 Automatic Re-Contouring Regions of Interest Based on Deformable Registration and Surface Reconstruction, AAPM 2004, (abstract: Medical Physics 31, 1845-6), (2004).

EP06795089 European Search Report, 7 pages, Dated Mar. 3, 2009.

Office Action from New Zealand Intellectual Property Office for Application 560988 dated Jul. 6, 2009 (2 pages).

* cited by examiner

METHOD AND APPARATUS FOR MODULATING A RADIATION BEAM

RELATED APPLICATIONS

This application claims priority to U.S. Provisional Patent Application No. 60/657,013, filed on Feb. 28, 2005, the entire content of which is incorporated herein by reference.

BACKGROUND

Intensity modulated radiation therapy ("IMRT") involves changing the size, shape, and intensity of a radiation beam to conform to the size, shape, and location of a patient's tumor. IMRT precisely targets the tumor while sparing surrounding normal tissue. Generally, IMRT is delivered using a radiation therapy system equipped with a radiation source and a linear accelerator ("linac"). The radiation beam exiting the linac travels through a multi-leaf collimator ("MLC") to change the size, shape, and intensity of the beam.

Prior to the development of the linac, radiation therapy machines used Cobalt-60 ("Co-60") as the radiation source. Co-60 radiation therapy machines use simple reliable technology that has been available since the 1950s. The Co-60 radioactive source is mounted in the radiation therapy machine. To deliver a dose to the patient, the radiation beam from the Co-60 source is collimated by jaws in a manner similar to that of the linac. Field shaping blocks may also be used to further shape the beam. Co-60 characteristics are stable and predictable, but generally require longer treatment times than the linac. Because the energy of Co-60 radiation is generally lower than that of a linac, Co-60 radiation therapy machines are normally only used to treat relatively shallow diseases such as those of the head and neck. Co-60 radiation therapy machines have not been retrofitted with a MLC, and MLC-based IMRT is not currently available with Co-60 radiation therapy machines.

SUMMARY

Development of the MLC has enhanced the delivery of radiation therapy treatment. The MLC defines the radiation beam to focus on the size, shape, and location of the patient's tumor. The MLC also modulates the radiation beam to minimize the amount of radiation delivered to normal tissues and organs surrounding the tumor.

The MLC includes a plurality of radiation blockers, called leaves. Each individual leaf in a MLC can be positioned independently allowing the user to create an infinite number of irregularly shaped fields. The radiation beams are directed between the ends of opposing arrays of the radiation blocking leaves, thereby shaping the radiation beam to closely match the shape of the tumor or target area, while shielding the normal tissues and organs from the direct radiation beam.

Other methods and apparatus for modulating the radiation beam include utilizing a plurality of radiation beam segments. Such methods and apparatus utilize attenuating leaves, or shutters, in a rack positioned in the path of the radiation beam before the beam enters the patient. The tumor is exposed to radiation in slices, each slice being selectively segmented by the leaves. However, a disadvantage of this method and apparatus results from the fact that only two slices of tissue volume may be treated with one rotation of the gantry. Although the slices may be of arbitrary thickness, greater resolution is accomplished by selecting slices for treatment that are as thin as possible. As the thickness of the treatment slice decreases, the time it takes to treat the patient increases because more treatment slices are required in order to treat the entire target volume.

Most modern linacs include a conventional MLC not originally designed for IMRT. Conventional MLC techniques provide limited dose conformality, based on the MLC design, number of beams and treatment time. IMRT machines require stringent position and speed tolerances that are limited by current collimator technology. Accordingly, there is a need for an improved collimator system and method for use on dynamic IMRT machines that improves dose conformality and resolution.

The present invention provides for multi-slice collimation radiation therapy within Co-60 or linac-based IMRT machines. It is a system and method for delivering IMRT by irradiating a treatment volume (containing multiple patient CT slices) with a single rotation of the radiation beam. The system includes a collimation device comprising a two-dimensional array of pivoting leaves, which are temporally placed into the radiation beam path as the gantry rotates around the patient. The two-dimensional array of pivoting leaves is positioned within a two-dimensional array of binary modulated slit apertures. The leaves are independently movable between a first state and a second state. The intensity of the radiation beam is modulated by controlling the time that each leaf is present in the slit aperture to attenuate the beam. In the present invention, multiple slices are irradiated simultaneously in a single gantry rotation.

In one embodiment, the invention provides a radiation therapy treatment system comprising a collimator including a plurality of leaf assemblies. Each of the leaf assemblies includes a support structure, a plurality of members supported by and extending from the support structure, and a plurality of leaves, each leaf supported by one of the members and adapted to move between a first position and a second position upon actuation. The arrangement of the leaf assemblies provides a two-dimensional array, the collimator operable to deliver radiation to a patient in a plurality of slices.

In another embodiment, the invention provides a radiation therapy treatment system comprising a gantry, a collimator, and a controller. The collimator is supported by the gantry and includes a plurality of leaf assemblies. Each leaf assembly includes a support structure, a plurality of members supported by and extending from the support structure, a plurality of leaves, each leaf supported by one of the members and adapted to move upon actuation, and a plurality of actuators, each actuator supported by one of the members and coupled to one of the leaves. The arrangement of the leaf assemblies provides a two-dimensional array and the controller is operable to selectively instruct the actuators to move the leaves to provide temporal and spatial modulation of a radiation beam.

In another embodiment, the invention provides a method of delivering radiation therapy treatment to a patient. The method comprises the acts of positioning the patient in a radiation therapy treatment system including a radiation source and a gantry operable to rotate around the patient, temporally and spatially modulating a radiation beam generated by the radiation source, and delivering a plurality of slices of radiation to the patient during a single rotation of the gantry.

In yet another embodiment, the invention includes a radiation therapy treatment system comprising a collimator and means for delivering a plurality of slices of radiation to a patient, the delivery means supported by the collimator.

The present invention makes clinical Co-60 IMRT possible, by using or incorporating IMRT into lower cost Co-60 radiation therapy machines. The present invention could be retro-fitted to existing Co-60 radiation therapy machines or linac-based radiation therapy machines.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use herein of "including," "comprising," or "having" and variations thereof is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first", "second", and "third" are used herein for purposes of description and are not intended to indicate or imply relative importance or significance.

In addition, it should be understood that embodiments of the invention include both hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

Figure 1:
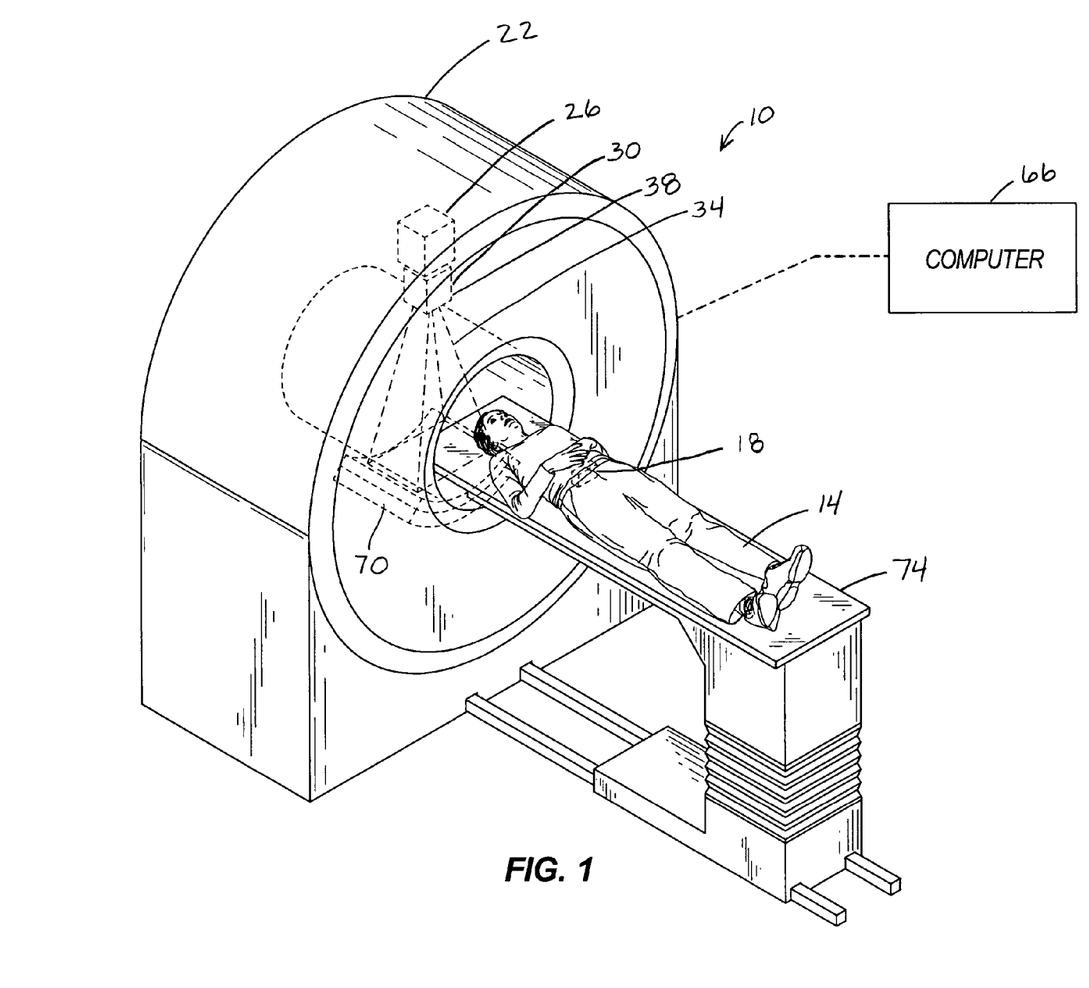
FIG. 1 is a perspective view of a radiation therapy treatment system.

FIG. 1 illustrates a radiation therapy treatment system 10 that can provide radiation therapy to a patient 14. Often, radiation is directed to a specific area or part of the patient 14, which is referred to and illustrated as a target 18. The radiation therapy treatment system 10 includes a gantry 22. Though the gantry 22 shown in the drawings is a ring gantry, i.e., it extends through a full 360° arc to create a complete ring or circle, other types of mounting arrangements may also be employed. For example, a C-type or partial ring gantry could be used. Any other framework capable of positioning the radiation source at various rotational and/or axial positions relative to the patient may also be employed.

The gantry 22 supports a radiation source 26. The radiation source 26 can include a linear accelerator 30 or a Co-60 source operable to generate a beam 34 of photon radiation. Other radiation sources may also be employed; for example, a Cobalt-60 radiation source, or any other source capable of delivering radiation of therapeutic or diagnostic benefit to the patient. The radiation source 26 can also include a modulation device 38 operable to modify or modulate the radiation beam 34. The modulation device 38 provides modulation needed to vary or modulate the intensity of photon radiation delivered to the patient 14. Such modulation is sometimes referred to as intensity modulated radiation therapy ("IMRT").

Figure 2:
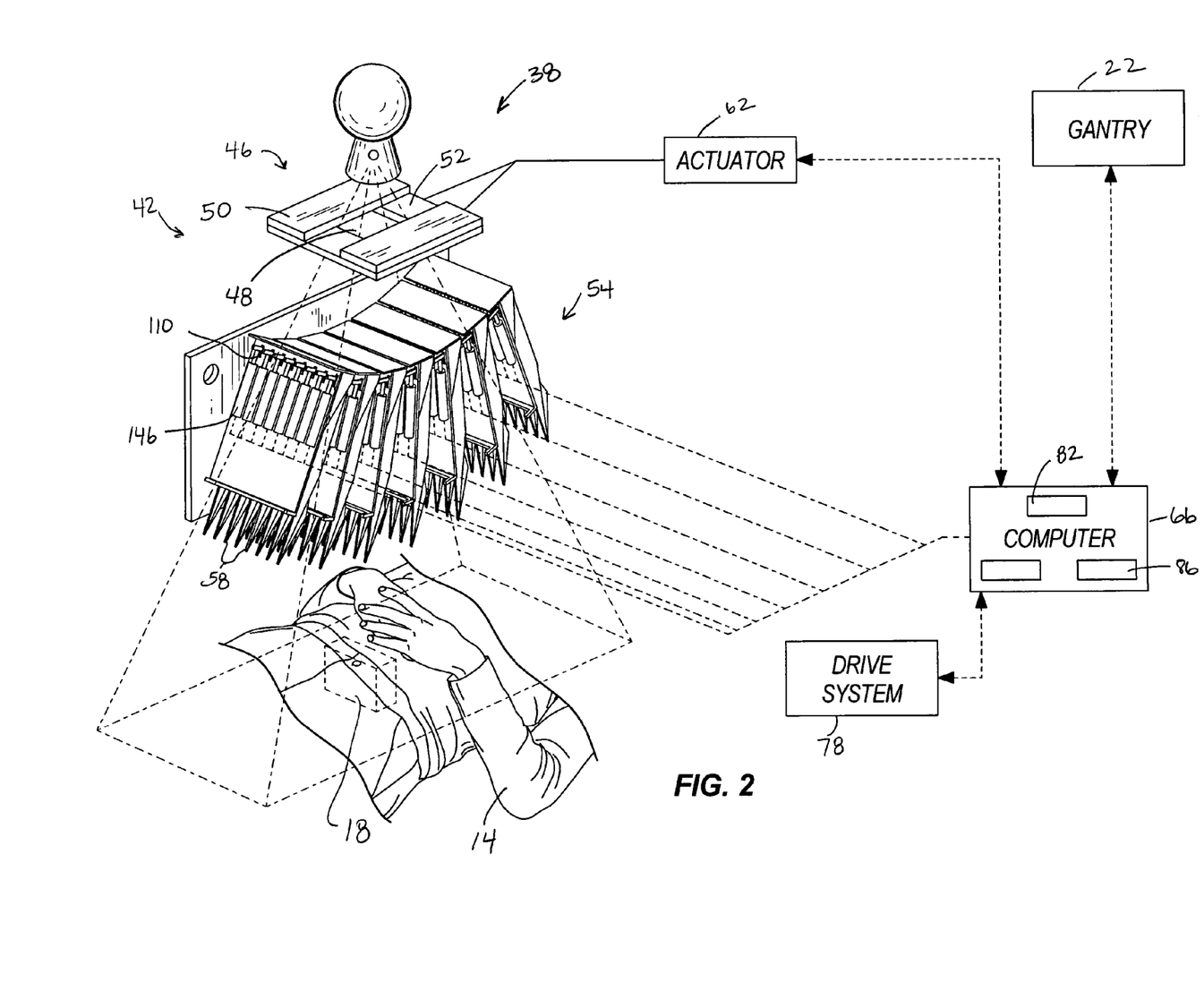
FIG. 2 is a perspective view of a multi-leaf collimator according to one embodiment of the invention that can be used in the radiation therapy treatment system illustrated in FIG. 1.

The modulation device 38 can include a collimation device 42 as illustrated in FIG. 2. The collimation device 42 includes a set of jaws 46 that define and adjust the size of an aperture 48 through which the radiation beam 34 may pass. The jaws 46 include an upper jaw 50 and a lower jaw 52. The upper jaw 50 and the lower jaw 52 are moveable to adjust the size of the aperture 48. The lower jaw 52 can also adjust the width of the beam 34 for a single slice.

The collimation device 42 also includes a plurality of leaf assemblies 54 operable to move between first and second positions to provide intensity modulation. Each of the leaf assemblies 54 includes a leaf 58, which can move between the first and second positions. The plurality of leaf assemblies 54 and jaws 46 modulate the intensity, size, and shape of the radiation beam 34 before the radiation beam 34 reaches the target 18. The jaws 46 are independently controlled by an actuator 62 (such as a motor, a pneumatic cylinder, a relay, a hydraulic cylinder, and the like) so that the size of the aperture 48 can be adjusted according to the treatment parameters. The actuator 62 can be controlled by a computer 66, controller, or similar device.

Generally, the thickness of the radiation beam slice is defined by the space between adjacent leaf assemblies 54. The slice thickness can be modified by closing the lower jaws 52 to a position that would define a narrower slice thickness than the space between adjacent leaf assemblies 54. The plurality of leaf assemblies 54 define a plurality of radiation beam slices and allow a plurality of the radiation beam slices to penetrate the target 18. One technique for delivering multi-slice radiation therapy is that each leaf assembly 54 would provide a treatment slice only until the area treated by an adjacent leaf assembly 54 is reached. For example, as the gantry 22 rotates around the target 18, the leaf assemblies 54 are sequentially activated to deliver its treatment slice. Alternatively, all (or some as prescribed) of the leaf assemblies 54 can be activated to deliver the treatment slice. Another technique for delivering multi-slice radiation therapy is defined for extended targets 18. Each leaf assembly 54 delivers a radiation slice to treat the entire target 18 volume as discussed below with respect to FIG. 9.

The radiation therapy treatment system 10 can also include a detector 70 (FIG. 1) operable to detect the radiation beam 34, a couch 74 to support the patient 14, and a drive system 78 operable to manipulate the location of the couch 74 based on instructions provided by the computer 66. The linear accelerator 30 or a Co-60 source and the detector 70 can also operate as a computed tomography (CT) system to generate CT images of the patient 14. The linear accelerator 30 emits the radiation beam 34 toward the target 18 in the patient 14. The target 18 and surrounding tissues absorb some of the radiation.

The CT images can be acquired with a radiation beam 34 that has a fan-shaped geometry, a multi-slice geometry, or a cone-beam geometry. In addition, the CT images can be acquired with the linear accelerator 30 or Co-60 source delivering megavoltage energies or kilovoltage energies. It is also noted that the acquired CT images can be acquired from the radiation therapy treatment system 10 or other image acquisition devices, such as other CT scanners, MRI systems, and PET systems. For example, previously acquired CT images for the patient 14 can include identified regions of interest and/or regions at risk. Newly acquired CT images for the patient 14 can be registered with the previously acquired CT images to assist in identifying the regions of interest and/or regions at risk in the new CT images.

In some embodiments, the radiation therapy treatment system 10 can include an x-ray source and a CT image detector. The x-ray source and the CT image detector operate in a similar manner as the linear accelerator 30 or a Co-60 source and the detector 70 to acquire image data. The image data is transmitted to the computer 66 where it is processed to generate cross-sectional images or "slices" of the patient's body tissues and organs.

The computer 66, illustrated in FIG. 2, includes an operating system 82 for running various software programs and/or communication applications. In particular, the computer 66 can include a software program or programs 86 that facilitate communication between the computer 66 and the radiation therapy treatment system 10 or other devices assisting in the radiation treatment process such as a laser positioning system or other computers. The computer 66 can include suitable input/output devices adapted to be accessed by medical personnel or technicians. The computer 66 can include typical hardware such as a processor, I/O interfaces, and storage devices or memory. The computer 66 can also include input devices such as a keyboard and a mouse. The computer 66 can further include output devices, such as a monitor. In addition, the computer 66 can include peripherals, such as a printer and a scanner.

According to one embodiment of the present invention, the collimation device 42, as illustrated in FIG. 2, includes a plurality of leaf assemblies 54 or leaf banks. The space between adjacent leaf assemblies 54 defines a path 90 (see FIG. 3) for the radiation beam 34. Only one leaf assembly 54 is described herein, however, it is noted that the description applies to each of the leaf assemblies 54. The leaf assembly 54 includes a support structure or frame 94 adapted to support a plurality of leaves 58. The leaves 58 are positioned generally adjacent to one another, but could include a space between adjacent leaves 58. In addition, the sides of the leaves 58 can be angled or tapered, for example, in a tongue and groove arrangement, to reduce potential radiation leakage between adjacent leaves. The collimator 42 and/or leaf assembly 54 can include a primary collimator 60 having radiation attenuation material (see FIG. 3) adapted to attenuate the radiation beam 34 and define the slice thickness. The radiation attenuation material can comprise tungsten, tungsten alloy or other suitable material. The radiation attenuation material 60 is positioned above the leaves 58 and can be positioned closer to the radiation source 26 than illustrated in FIG. 3. It is noted that the attenuation material 60 is arranged to diverge with respect to the radiation source 26. For example, the attenuation material 60 generally follows the divergence of the leaf assemblies as illustrated in FIG. 2.

Figure 3:
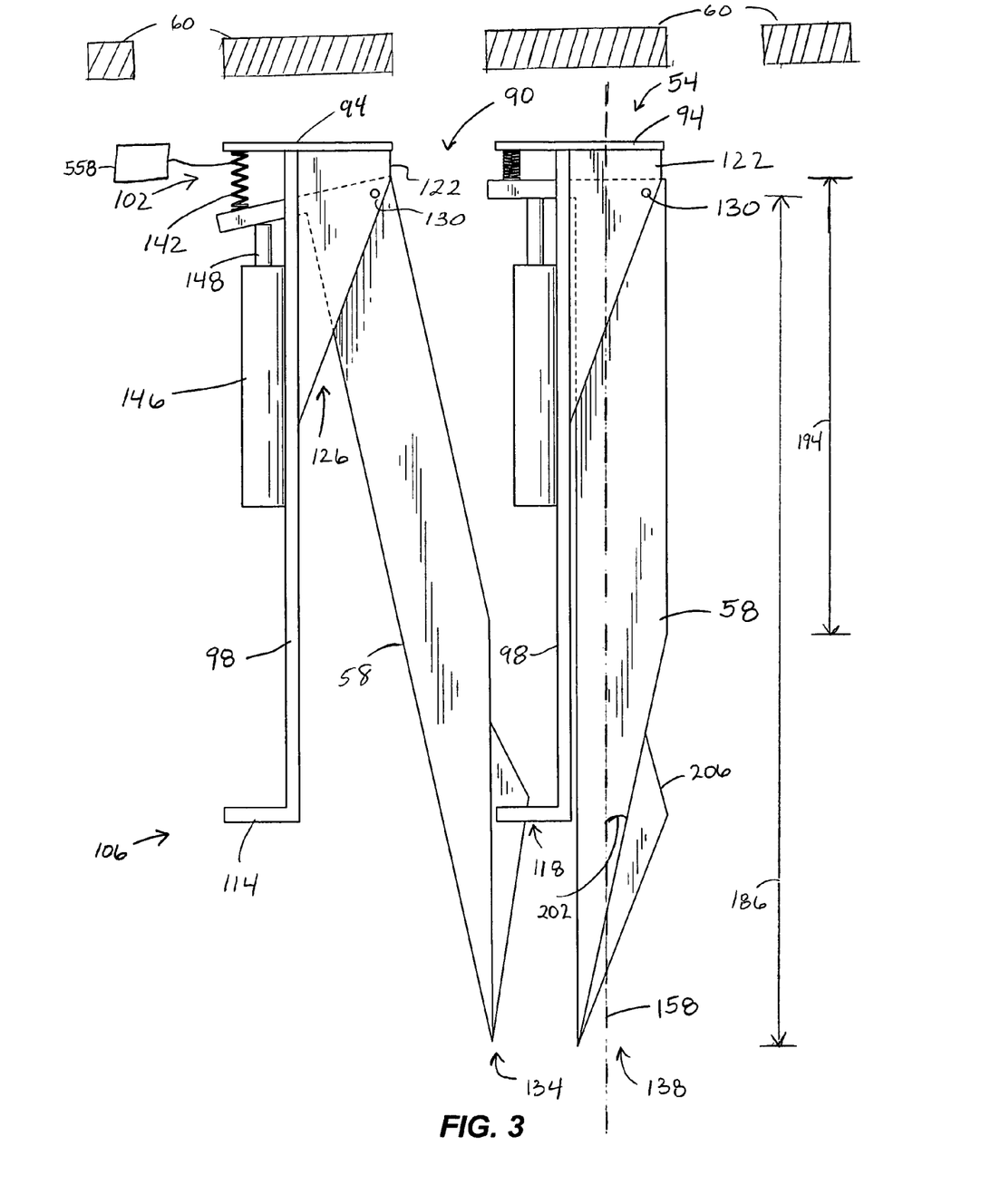
FIG. 3 is a side view of the multi-leaf collimator of FIG. 2.

As shown more clearly in FIG. 3, the leaf assembly 54 includes a wall or a member 98 extending in a generally downward direction from the frame 94. The member 98 includes a first end 102 and a second end 106. The member 98, near the first end 102, includes a plurality of apertures 110 (see FIG. 2), each adapted to receive at least a portion of one of the leaves 58 (described below). The member 98, near the second end 106, includes a lip 114 adapted to extend in a direction substantially perpendicular to the member 98. The lip 114 extends the length of the member 98 and includes a plurality of slits 118. Each slit 118 is adapted to receive at least a portion of one of the leaves 58. The frame 94, the member 98, and the lip 114 can be comprised of steel or other suitable material.

The leaf assembly 54 can also include a plurality of leaf guides 122 coupled to the frame 94 and the member 98. The leaf guides 122 are arranged near the first end 102 and along the length of the member 98 with a space between adjacent leaf guides 122. Each leaf guide 122 includes a recess 126 adapted to receive at least a portion of one of the leaves 58. The leaf guide 122 includes a shaft 130 adapted to receive a leaf 58 such that the leaf 58 pivots about the shaft 130.

Each leaf 58 is adapted to pivot about its respective shaft 130 from a first position 134 to a second position 138. For example, a leaf 58 can pivot from the first position 134 (a closed position) to the second position 138 (an open position) or to a position between the first position 134 and the second position 138. The leaves 58 can be comprised of tungsten, a tungsten alloy, or other suitable material.

The leaf 58 is biased toward the first position 134, e.g., a closed position, with a biasing device 142, such as a spring or other elastic device. The biasing device 142 is coupled to the frame 94 and extends in a direction generally parallel with the member 98. The biasing device 142 exerts a generally downward force on the leaf 58 that causes the leaf 58 to pivot about the shaft 130 to the first position 134 (a closed position). The positioning of the leaf 58 is controlled by an independent actuator 146 (such as a motor, a pneumatic cylinder, a solenoid, a hydraulic cylinder, and the like) to permit or block the passage of radiation. In this construction, the actuator 146 is a pneumatic cylinder having a piston moved by air pressure. In other constructions, the actuator 146 can include electromechanical or hydraulic means to move the leaf 58.

As illustrated in FIGS. 2 and 3, the actuator 146 includes a piston 148, which moves in a direction generally parallel with the member 98 to apply an upwardly directed force to the leaf 58. This force compresses the biasing device 142 and moves the leaf 58 in a direction toward the second position 138 or a position between the first position 134 and the second position 138. The upward force of the piston 148 on the leaf 58 causes the path 90 to open and allow the radiation beam 34 through the path 90. The radiation beam 34 is modulated based on the position of each of the leaves 58 in the collimation device 42.

Each of the actuators 146 is controlled by the computer 66. The computer 66 receives input, via the software program 86, regarding the patient's treatment plan, which includes the prescription for the radiation dose. The computer 66 processes the treatment plan to determine the position and timing of each of the leaves 58 and corresponding actuators 146 as the gantry 22 rotates around the patient 14. For example, in the construction illustrated in FIGS. 2 and 3, the computer 66 instructs one of the actuators 146 to move a certain distance and to remain in a certain position for a predetermined period of time such that the corresponding leaf 58 moves from the first position 134 to a second position 138 to allow passage of the radiation beam 34 through the respective path 90 based on the prescribed dose and gantry location.

Figure 4A:
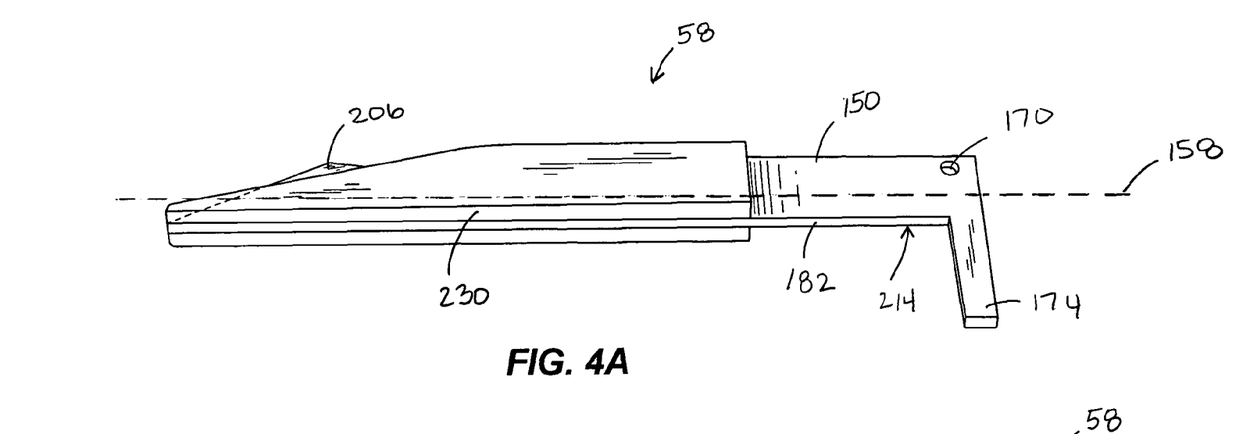
FIGS. 4A-B illustrate views of a leaf of the multi-leaf collimator of FIG. 2.
Figure 4B:
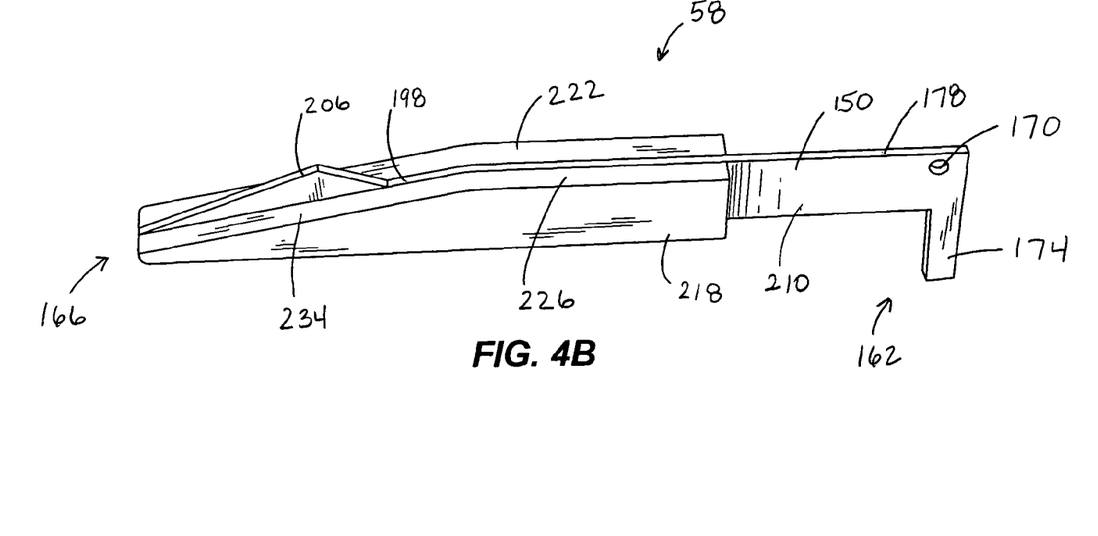

With reference to FIGS. 3, 4A, and 4B, the leaf 58 includes a first portion 150, which includes an axis 158 that extends generally parallel with the member 98 when the leaf 58 is positioned on the shaft 130 of the leaf guide 122 and in the second position 138. The first portion 150 includes a first end 162 and a second end 166 (see FIG. 4B). The first end 162 includes an aperture 170 adapted to receive the shaft 130 of the leaf guide 122 and an extension 174 that extends in a direction generally perpendicular to the axis 158 of the first portion 150.

The first portion 150 includes an upper surface 178 generally oriented to be parallel with the axis 158 and a lower surface 182 generally oriented to be parallel with the axis 158. The lower surface 182 is in contact or substantial contact with the member 98 when the leaf 58 is in the second position 138. The lower surface 182 includes a length 186 and extends beyond the lip 114 of the member 98. The length 186 of the lower surface 182 of each of the leaves 58 can vary with respect to one another. The upper surface 178 includes a length 194 generally less than the length 186 of the lower surface 182 of the leaf 58. The length 194 of the upper surface 178 of each leaf 58 can vary with respect to one another. The first portion 150 further includes a surface 198 that connects the upper surface 178 and the lower surface 182. The surface 198 is oriented at an angle 202 with respect to the axis 158. The angle 202 can be in the range of about 10 degrees to about 75 degrees. The surface 198 includes a member 206 that extends outwardly from at least a portion of the surface 198. The member 206 is adapted to be received in the slit 118 of the lip 114 of an adjacent leaf assembly 54 when the leaf 58 is in the first position 134.

The first portion 150 of the leaf 58 also includes a front surface 210 and a rear surface 214. The leaf 58 includes a front member 218 coupled to the front surface 210 and a rear member 222 coupled to the rear surface 214. The front member 218 is further described herein with respect to the front surface 210, and the rear member 222 is not further discussed, however, it is noted that the rear member 222 is similarly arranged with respect to the rear surface 214.

The front member 218 includes an upper surface 226 generally coplanar with respect to the upper surface 178 of the first portion 150 of the leaf 58. For example, the upper surface 226 of the front member 218 is generally parallel with respect to the axis 158 of the leaf 58. The front member 218 also includes a lower surface 230 generally coplanar with respect to the lower surface 182 of the first portion 150 of the leaf 58. For example, the lower surface 230 of the front member 218 is generally parallel with respect to the axis 158 of the leaf 58. The front member 218 further includes a surface 234 that connects the upper surface 226 and the lower surface 230 and is generally coplanar with respect to the surface 198 of the first portion 150 of the leaf 58. In other constructions of the leaf 58, the upper surface 226, the lower surface 230, and the surface 234 of the front member 218 can extend beyond respective upper surface 178, lower surface 182, and surface 198 of the first portion 150 such that the upper surface 226, the lower surface 230, and the surface 234 of the front member 218 are not coplanar with respect to the upper surface 178, lower surface 182, and surface 198 of the first portion 150, respectively.

As illustrated in FIGS. 4A and 4B, the leaf 58 appears to include three components, the first portion 150, the front member 218, and the rear member 222, however, in some constructions, the leaf 58 is constructed as a single component. The leaf 58 is comprised of tungsten, a tungsten alloy, or other suitable material.

Figure 5A:
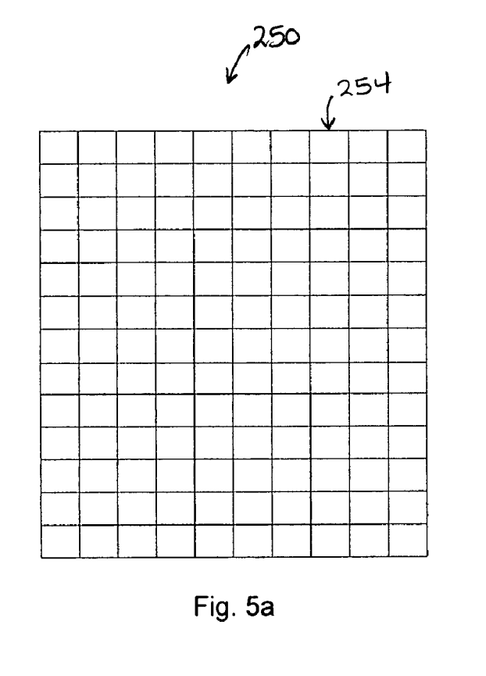
FIGS. 5A-C schematically illustrate an array of leaves of the multi-leaf collimator of FIGS. 2 and 6-8.
Figure 5B:
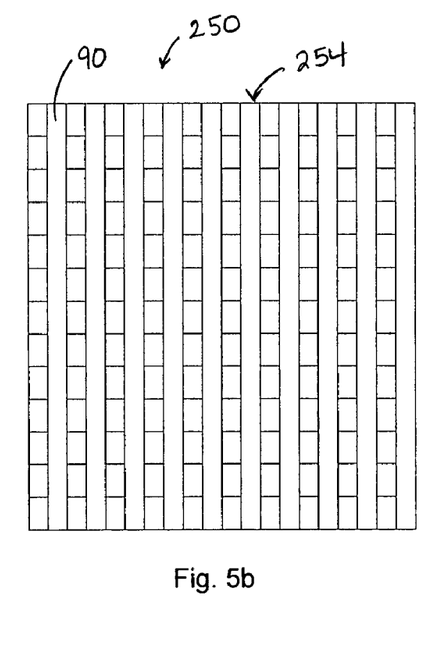
Figure 5C:
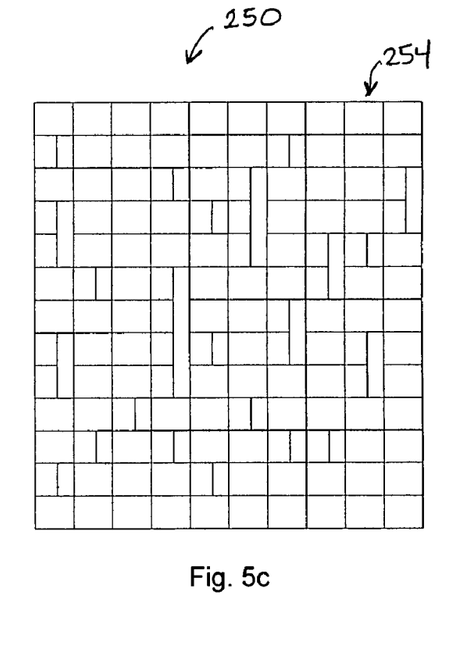

The plurality of leaf assemblies 54 create an array 250 of radiation paths 90 (beamlets) as illustrated in FIGS. 5A-C. The array 250 of radiation paths 90 provide temporal and spatial modulation of the radiation source 26. The array 250 of paths 90 can deliver radiation treatment to the patient 14 in a plurality of slices. A single slice 254 is defined by the paths 90 of the adjacent leaves 58 of a single leaf assembly 54. The FIGS. 5A-C illustrate a single slice 254 as a vertical column and a leaf assembly 54 as a column in the array 250. Specifically, FIG. 5A illustrates an array of leaf assemblies 54 with each leaf 58 in the first position 134 (i.e., closed). FIG. 5B illustrates an array of leaf assemblies 54 with each leaf 58 in the second position 138 (i.e., open). FIG. 5C illustrates an array of leaf assemblies 54 with some leaves 58 in the first position 134 and some of the leaves 58 in the second position 138.

Figure 6:
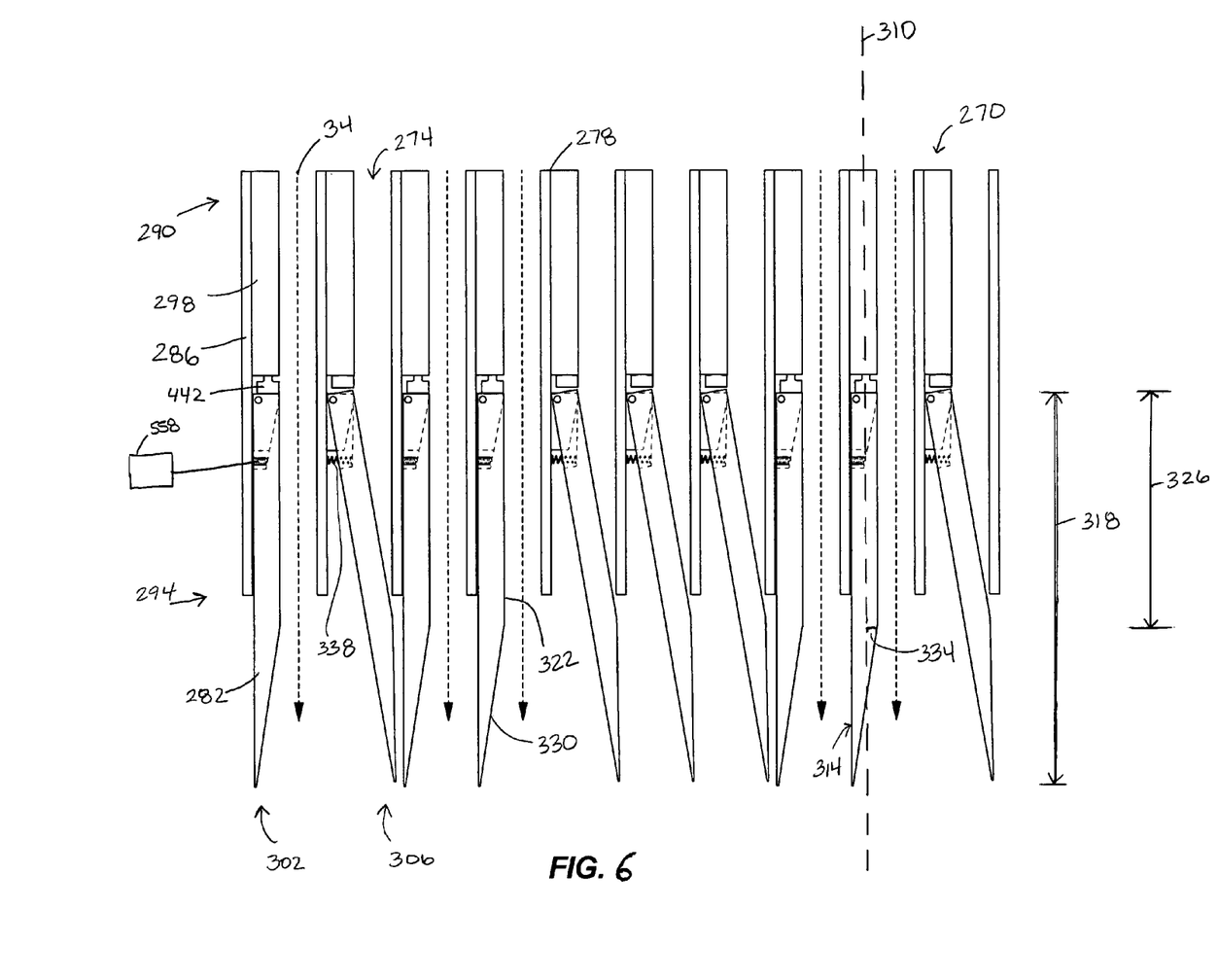
FIG. 6 is a side view of another construction of the multi-leaf collimator of FIG. 2.

FIG. 6 illustrates another independent construction of the collimation device 42. The collimation device 42 includes a plurality of leaf assemblies 270 or leaf banks. The space between adjacent leaf assemblies 270 defines a path 274 for the radiation beam 34. Only one leaf assembly 270 is described herein, however, it is noted that the description applies to each of the leaf assemblies 270. The leaf assembly 270 includes a support structure or frame 278 adapted to support a plurality of leaves 282. The leaves 282 are positioned generally adjacent to one another, but a space could separate adjacent leaves 282.

The leaf assembly 270 includes a wall or a member 286 extending in a generally downward direction from the frame 278. The member 286 includes a first end 290 and a second end 294. The member 286, near the first end 290, includes an actuator 298 adapted to move the leaf 282 from a first position 302 (e.g., an open position) to a second position 306 (e.g., a closed position) or a position between the first position 302 and the second position 306. The frame 278 and the member 286 can be comprised of steel or other suitable material.

The leaf 282 includes an axis 310 that extends generally parallel with the member 286. The leaf 282 includes a first surface 314 generally oriented to be parallel with the axis 310 and the member 286 when the leaf 282 is in the first position 302. The first surface 314 is in contact or substantial contact with the member 286 while the leaf 282 is in the first position 302. The first surface 314 includes a length 318 that extends beyond second end 294 of the member 286. The length 318 of the first surface 314 of each of the leaves 282 can vary with respect to one another. The leaf 282 also includes a second surface 322 generally oriented to be parallel with the axis 310 and member 286 and is opposite the first surface 314. The second surface 322 includes a length 326 generally less than the length 318 of the first surface 314 of the leaf 282. The length 326 of the second surface 322 of each leaf 282 can vary with respect to one another. The second surface 322 is adapted to make contact with or substantial contact with a member 286 of an adjacent leaf assembly 270. The leaf 282 further includes a third surface 330 that connects the first surface 314 and the second surface 322. The third surface 330 is oriented at an angle 334 with respect to the axis 310.

The leaf 282 is biased toward the second position 306, e.g., a closed position or the second surface 322 in substantial contact with an adjacent member 286, with a biasing device 338, such as a spring or other elastic device. The positioning of the leaf 282 is controlled by the actuator 298. In this construction, the actuator 298 is a pneumatic cylinder having a piston moved by air pressure. In other constructions, the actuator 298 can include electromechanical or hydraulic means to move the leaf 282. As illustrated in FIG. 6, the actuator 298 includes a piston 442, which moves in a direction generally parallel with the member 286 to apply a downwardly directed force to the leaf 282, which compresses the biasing device 338 and moves the leaf 282 in a direction toward the first position 302 or a position between the first position 302 and the second position 306. The downward force of the piston 442 on the leaf 282 causes the path 274 to open and allow the radiation beam 34 through the path 274. The radiation beam 34 is modulated based on the position of each of the leaves 282 in this construction of the collimation device 42.

Each of the actuators 298 is controlled by the computer 66. The computer 66 receives input, via the software program 86, regarding the patient's treatment plan, which includes the prescription for the radiation dose. The computer 66 processes the treatment plan to determine the position and timing of each of the leaves 282 and corresponding actuators 298 as the gantry 22 rotates around the patient 14. For example, in the construction illustrated in FIG. 6, the computer 66 instructs one of the actuators 298 to move a certain distance along the axis 310 and to remain in a certain position for a predetermined period of time such that the corresponding leaf 282 moves from the second position 306 to a first position 302 to attenuate the radiation beam 34 traveling through the respective path 274 based on the prescribed dose and gantry location.

The plurality of leaf assemblies 270 creates an array 250 of radiation paths 274 (beamlets) as illustrated in FIGS. 5A-C. The array 250 of radiation paths 274 provides temporal and spatial modulation of the radiation source 26. The array 250 of paths 274 can deliver radiation treatment to the patient 14 in a plurality of slices. A single slice 254 includes a path 274 from each leaf 282 at the same respective position of each leaf assembly 270. For example, a single slice 254 is defined by the paths 274 of the first leaf 282 of each leaf assembly 270. FIGS. 5A-C illustrate a single slice 254 as a horizontal row and a leaf assembly 270 as a column in the array 250. Specifically, FIG. 5A illustrates an array of leaf assemblies 270 with each leaf 282 in the second position 306. FIG. 5B illustrates an array of leaf assemblies 270 with each leaf 282 in the first position 302. FIG. 5C illustrates an array of leaf assemblies 270 with some leaves 282 in the first position 302 and some of the leaves 282 in the second position 306.

Figure 7:
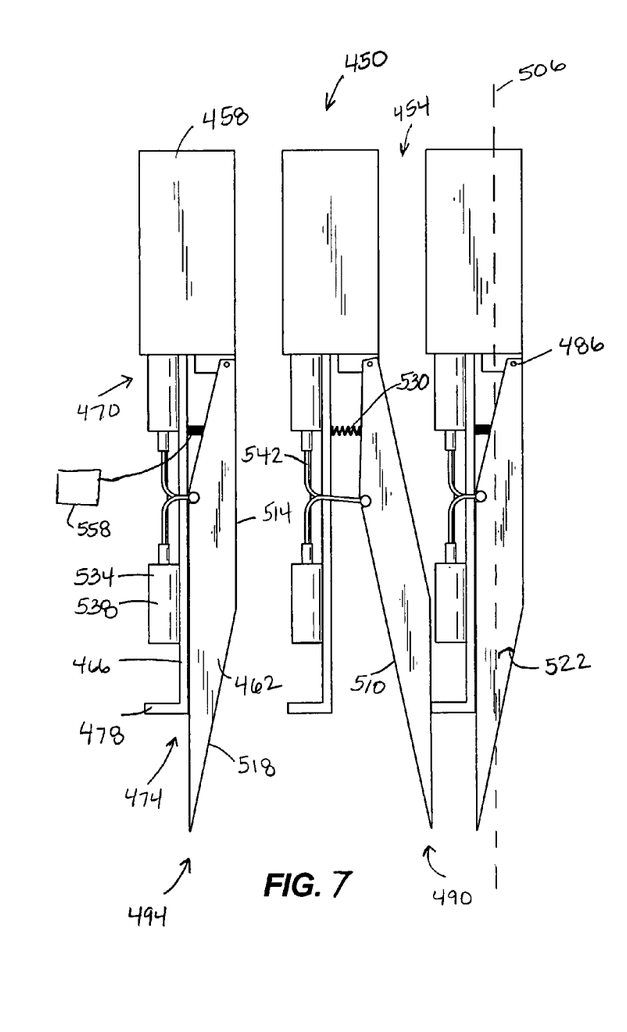
FIG. 7 is a side view of another construction of the multi-leaf collimator of FIG. 2.
Figure 8:
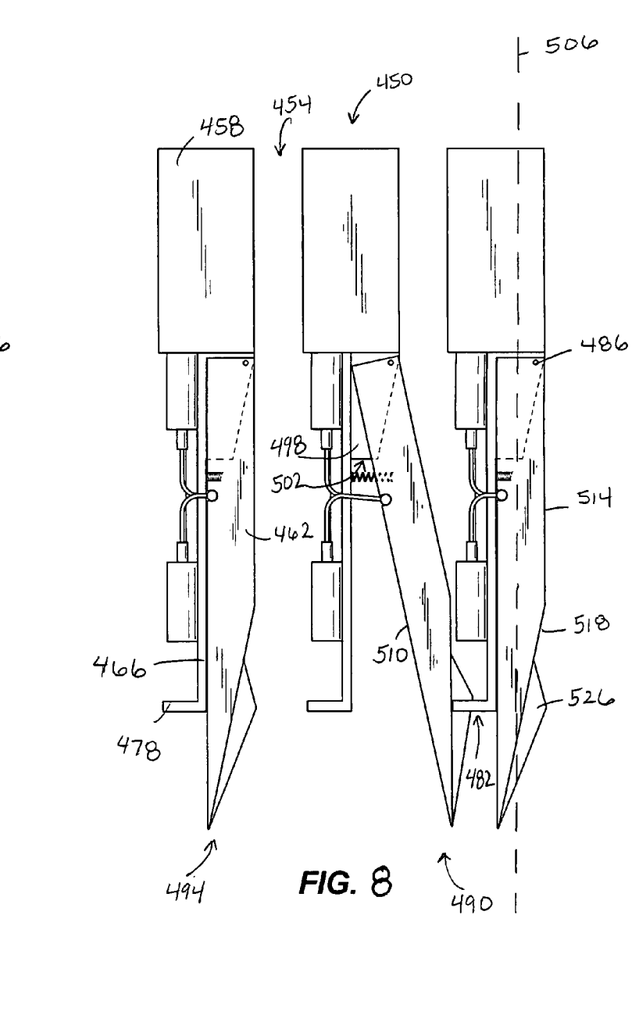
FIG. 8 is a side view of another construction of the multi-leaf collimator of FIG. 2.

FIGS. 7 and 8 illustrate another construction of the collimation device 42. In this construction, the collimation device 42 includes a plurality of leaf assemblies 450. The space between adjacent leaf assemblies 450 defines a path 454 for the radiation beam 34. Each leaf assembly 450 or leaf bank includes a support structure or frame 458 adapted to support a plurality of leaves 462. The leaves 462 are positioned generally adjacent to one another, but a space could separate adjacent leaves 462.

The leaf assembly 450 includes a wall or a member 466 extending in a generally downward direction from the frame 458. The member 466 includes a first end 470 and a second end 474. The member 466, near the second end 474, includes a lip 478 adapted to extend in a direction substantially perpendicular to the member 466. As illustrated in FIG. 8, the lip 478 can extend the length of the member 466 and, in some constructions, includes a plurality of slits 482. Each slit 482 is adapted to receive at least a portion of one of the leaves 462. The frame 458, the member 466, and the lip 478 can be comprised of steel or other suitable material.

The leaf assembly 450 includes a shaft 486 coupled to the frame 458. Each leaf 462 is adapted to pivot about its respective shaft 486 from a first position 490 to a second position 494. For example, a leaf 462 can pivot from the first position 490 (a closed position) to the second position 494 (an open position) or to a position between the first position 490 and the second position 494. The leaves 462 can be comprised of tungsten or other suitable material.

In some constructions, the leaf assembly 450 can include a plurality of leaf guides 498 (FIG. 8) coupled to the frame 458 and the member 466. The leaf guides 498 are arranged near the first end 470 and along the length of the member 466 with a space between adjacent leaf guides 498. Each leaf guide 498 includes a recess 502 adapted to receive at least a portion of one of the leaves 462. The leaf guide 498 is adapted to support and guide the position of the leaf 462 as it moves from a first position 490 to a second position 494 or any position between the first position 490 and the second position 494.

The leaf 462 includes an axis 506 that extends generally parallel with the member 466 when the leaf is positioned in the second position 494. The leaf 462 includes a first surface 510 generally oriented to be parallel with the axis 506 and the member 466 when the leaf is positioned in the second position 494. The first surface 510 is in contact or substantial contact with the member 466. The first surface 510 extends beyond the second end 474 of the member 466. The leaf 462 also includes a second surface 514 generally oriented to be parallel with the first surface 510. The length of the first surface 510 and the second surface 514 of each leaf 462 can vary with respect to one another. The leaf 462 further includes a third surface 518 that connects the first surface 510 and the second surface 514. The third surface 518 is oriented at an angle 522 with respect to the axis 506.

In some constructions, the third surface 518 can include a member 526 or second leaf guide that extends outwardly from at least a portion of the surface 518. The member 526 is adapted to be received in the slit 482 of the lip 478 of an adjacent leaf assembly 450 when the leaf 462 is in the first position 490. The member 526 is adapted to support and guide the position of the leaf 462 as it moves from a first position 490 to a second position 494 or any position between the first position 490 and the second position 494.

The leaf 462 is biased toward the first position 490, e.g., a closed position, with a biasing device 530, such as a spring or other elastic device. The positioning of the leaf 462 is controlled by an independent actuator 534. The actuator 534 in this construction includes a pull-type solenoid 538 and can include more than one pull-type solenoid. The solenoid 538 includes a link 542 or plunger coupled to the leaf 462. The link 542 can be coupled to the leaf 462 near the first surface 510 of the leaf 462. The pull-type solenoid 538 operates to apply a force or pull the leaf 462 toward the second position 494 (e.g., toward the member 466) with the link 542 when a magnetic field is generated. The generation of the magnetic field causes the leaf 462 to open the path 454 for passage of the radiation beam 34. When the magnetic field is deactivated, the biasing device 530 applies a force to the leaf 462 and pushes the leaf 462 toward the first position 490 (e.g., toward the member 466 of the adjacent leaf assembly 450). The radiation beam 34 is modulated based on the position of each leaf 462.

Each of the actuators 534 is controlled by the computer 66. The computer 66 receives input, via the software program 86, regarding the patient's treatment plan, which includes the prescription for the radiation dose. The computer 66 processes the treatment plan to determine the position and timing of each of the leaves 462 and corresponding actuators 534 as the gantry 22 rotates around the patient 14. For example, in the construction illustrated in FIGS. 7 and 8, the computer 66 instructs one of the solenoids 538 to generate a magnetic field or to deactivate the magnetic field for a predetermined period of time such that the corresponding leaf 462 moves from the first position 490 to the second position 494 to attenuate the radiation beam 34 traveling through the respective paths 454 based on the prescribed dose and gantry location.

The plurality of leaf assemblies 450 creates an array 250 of radiation paths 454 (beamlets) as illustrated in FIGS. 5A-C. The array 250 of leaf assemblies 450 can deliver radiation treatment to the patient 14 in a plurality of slices 254. The array 250 of radiation paths 454 provide temporal and spatial modulation of the radiation source 26. A single slice 254 includes a path 454 from each leaf 462 at the same respective position of each leaf assembly 450. For example, a single slice 254 is defined by the paths 454 of the first leaf 462 of each leaf assembly 450. The FIGS. 5A-C illustrate a single slice 254 as a horizontal row and a leaf assembly 450 as a column in the array 250. Specifically, FIG. 5A illustrates an array of leaf assemblies 450 with each leaf 462 in the first position 490. FIG. 5B illustrates an array of leaf assemblies 450 with each leaf 462 in the second position 494. FIG. 5C illustrates an array of leaf assemblies 450 with some leaves 462 in the first position 490 and some of the leaves 462 in the second position 494.

In some constructions of the collimation device 42, a sensor 558 or a plurality of sensors can be employed with each of the leaves 58, 282, and 462 of the respective leaf assemblies 54, 270, and 450. The sensor 558 can detect the deflection amount of the biasing device 142, 338, and 530 to determine whether the leaf 58, 282, and 462 is open, closed, opening, or closing. The sensor 558 could also be positioned to detect movement of the piston and/or actuator to determine whether the leaf 58, 282, and 462 is open, closed, opening, or closing.

Figure 9:
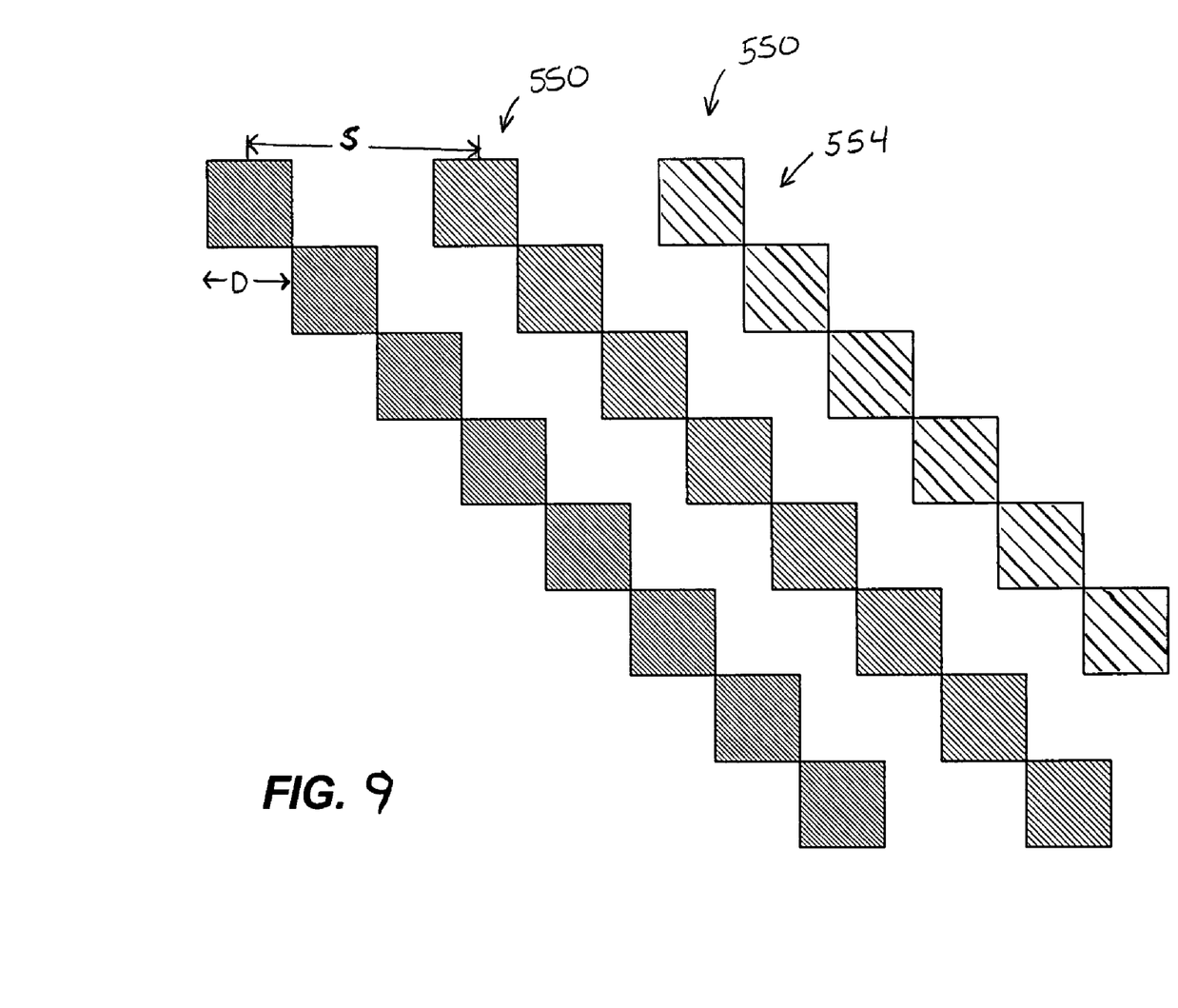
FIG. 9 schematically illustrates a method for radiation delivery using the multi-leaf collimator of FIG. 2.

FIG. 9 schematically illustrates a method for radiation delivery using the collimation device 42 of the present invention. The collimation device 42 includes a plurality of leaf assemblies 550 (each leaf assembly 550 represented by one of the shaded boxes in each row), each leaf assembly 550 including a plurality of leaves 554. The leaf assemblies 550 are oriented in a plurality of rows and, the leaf assembly 550 of one row is offset with respect to a leaf assembly 550 of an adjacent row. The leaf assemblies 550 can be in the form of the leaf assemblies 54, 270, or 450 as described above. Likewise, the leaves 554 can be in the form of the leaves 58, 282, or 462 as described above. Each leaf assembly 550 defines a radiation path with a different divergence from the radiation source.

The distance (S) between leaf assemblies 550 at the axis of gantry rotation, the radiation slice width (w) and the distance of couch travel per gantry rotation (D) may be adjusted to achieve optimal radiation delivery with minimal junctioning effects between the slices. Pitch is the couch travel distance for a complete gantry rotation relative to the axial beam width at the axis of rotation. By selecting an appropriate spacing between slices (S) and slice width (w), radiation can be delivered for extended distances with a real pitch of one and a virtual pitch of less than one, if the distance D is set equal to w. This method for radiation delivery can minimize dose ripple since this avoids junctioning effects produced by the different divergences of the leaf assemblies 550. For example, for a three slice collimator, if the couch distance (D) traveled per rotation is set equal to the selected slice width (w), and the slice spacing (S) is chosen as defined by equation 1, $$S = 2\tfrac{2}{3} \times w \qquad \text{Equation 1}$$

then a delivery with a virtual pitch of ⅓ will be created (i.e., each position in the patient will be irradiated by each of the three collimated slices). This applies to slices beyond the distal leaf assembly 550.

The embodiment illustrated in FIG. 9 can be used with extended target distances. Each leaf assembly 550 provides a treatment slice that penetrates the entire target volume. In this embodiment, the lower jaws 52 move to define which leaf assemblies 550 are allowed to irradiate the patient 14, and the selected leaf assemblies 550 deliver the radiation slices to the target 18 as the gantry 22 rotates.

The collimation device 42 in any one of the various constructions described above can be used with a Co-60 radiation therapy machine to provide intensity modulation radiation therapy. Also, linac-based IMRT machines could use lower doses or shorter treatment times. It also allows for the use of overlapping fields (shift patient) or offset units to treat larger volumes. One-hundred-eighty degree collimator rotation may be used for better resolution in the plane of rotation. A tongue and groove connection between the leaves may be incorporated to reduce leakage between the leaves. Also, multi-slice collimation radiation therapy may be a viable option as a dedicated unit for specific sites (e.g. head and neck), representing a significant fraction of a radiology department's workload.

Various features and advantages of the invention are set forth in the following claims.

What is claimed is:

1. A radiation therapy treatment system comprising:
    a collimator including a plurality of leaf assemblies, each leaf assembly having
        a support structure,
        a plurality of leaves coupled to the support structure and adapted to pivot with respect to the support structure, and
        an unobstructed pathway extending from one leaf to an adjacent leaf, and
    wherein the arrangement of the leaf assemblies provides a two-dimensional array, the collimator configured to separate a megavoltage radiation beam into a plurality of independent beamlets, and
    further wherein each independent beamlet is defined by only a single leaf.

2. The system of claim 1 further comprising an actuator coupled to the leaf, the actuator operable to selectively actuate the leaf to move between a first position and a second position.

3. The system of claim 2 further comprising a gantry and a controller operable to selectively instruct the actuator to move the leaf between the first position and the second position based on a radiation treatment plan and a position of the gantry.

4. The system of claim 1 wherein at least one leaf is adapted to move between a first position and a second position, and wherein one of the first position and the second position is a closed position and the other one of the first position and the second position is an open position.

5. The system of claim 4 wherein when the leaf is in one of the first position and the second position, the leaf is operable to block radiation and when the leaf is in the other one of the first position and the second position, the leaf generates a path for the passage of radiation.

6. The system of claim 1 further comprising means for biasing the leaf to a closed position.

7. The system of claim 1 wherein the collimator further comprises attenuation material positioned above the leaves.

8. The system of claim 1 wherein the leaves are arranged vertically in the array.

9. The system of claim 8 wherein the arrangement of the leaf assemblies and the leaves provides a two-dimensional array to provide temporal and spatial modulation of a radiation beam.

10. The system of claim 1 wherein the leaf includes a member that extends outwardly therefrom, and wherein the member engages a slit of an adjacent leaf assembly when the leaf is in a closed position.

11. The system of claim 1 wherein each of the leaf assemblies are oriented in a plurality of rows, and wherein the leaf assembly of one row is offset with respect to a leaf assembly of an adjacent row.

12. The system of claim 11 wherein the offset arrangement of the leaf assemblies provides a gap between the leaf assemblies in a single row.

13. A radiation therapy treatment system comprising:
a gantry;
a collimator supported by the gantry, the collimator including a plurality of leaf assemblies, each leaf assembly including
a support structure,
a plurality of leaves coupled to the support structure and adapted to pivot with respect to the support structure,
an unobstructed pathway extending from one leaf to an adjacent leaf,
a plurality of actuators, each actuator coupled to one of the leaves, and
wherein the arrangement of the leaf assemblies provides a two-dimensional array, the collimator configured to separate a megavoltage radiation beam into a plurality of independent beamlets, and
further wherein each independent beamlet is defined by only a single leaf; and
a controller operable to selectively instruct the actuators to move the leaves to provide temporal and spatial modulation of the megavoltage radiation beam.

14. The system of claim 13 wherein the controller instructs an actuator to move a respective leaf based on a radiation treatment plan and a position of the gantry.

15. The system of claim 13 wherein the actuator is adapted to actuate the leaf and move the leaf between a first position and a second position.

16. The system of claim 15 wherein one of the first position and the second position is a closed position and the other one of the first position and the second position is an open position.

17. The system of claim 13 wherein the collimator is operable to deliver radiation to a patient in a plurality of slices.

18. The system of claim 13 wherein the leaves are arranged to diverge in the array with respect to a radiation source supported by the gantry.

19. The system of claim 13 wherein the leaves are arranged vertically in the array.

20. A radiation therapy treatment system comprising:
a collimator; and
means for delivering a plurality of independently controlled slices of megavoltage radiation to a patient at substantially the same time, the delivery means supported by the collimator.

21. The system of claim 20 further comprising a gantry and wherein the plurality of slices of radiation are delivered to the patient during a single gantry rotation.

22. The system of claim 20 wherein the delivery means includes a plurality of leaves operable to pivot between a first position and a second position.

23. A radiation delivery system comprising:
a collimator including a first leaf assembly and a directly-adjacent second leaf assembly, the first leaf assembly including
a first support structure,
a plurality of leaves coupled to the first support structure and adapted to pivot with respect to the first support structure, and
a first radiation pathway between the first leaf assembly and the directly-adjacent second leaf assembly, the first radiation pathway being unobstructed between adjacent leaves,
the second leaf assembly including
a second support structure,
a plurality of leaves coupled to the second support structure and adapted to pivot with respect to the second support structure, and
a second radiation pathway defined on a side of the second leaf assembly opposite to the first radiation pathway, the second radiation pathway being unobstructed between adjacent leaves, and
wherein the leaf assemblies are adapted to attenuate megavoltage radiation.

24. A radiation delivery system comprising:
a plurality of leaf assemblies, each leaf assembly including
a support structure, and
a plurality of leaves coupled to the support structure and adapted to pivot with respect to the support structure; and
a plurality of separate pathways, each pathway oriented between adjacent leaf assemblies, and each pathway being independently controlled by at least one leaf of only one of the leaf assemblies, and wherein the leaf assemblies are adapted to attenuate megavoltage radiation.

* * * * *